United States Patent [19]

Mauldin et al.

[11] Patent Number: 4,751,920

[45] Date of Patent: Jun. 21, 1988

[54] PIVOTING KNEE BRACE WITH ROTATING AND TRANSLATING TIBIA COLLAR

[75] Inventors: Donald M. Mauldin; Richard E. Jones, both of Dallas; Dwain R. Faso, Allen, all of Tex.

[73] Assignee: 3D Orthopedic, Inc., Dallas, Tex.

[21] Appl. No.: 4,970

[22] Filed: Jan. 20, 1987

[51] Int. Cl.⁴ .............................. A61F 5/01; A61F 5/37
[52] U.S. Cl. .................................. 128/80 C; 128/80 F
[58] Field of Search ...................... 128/88, 80 C, 80 F, 128/80 G

[56] References Cited

U.S. PATENT DOCUMENTS

| | | | |
|---|---|---|---|
| 1,477,070 | 12/1923 | Martin | 128/88 |
| 2,460,895 | 2/1949 | Meany | 128/80 C |
| 3,945,046 | 3/1976 | Stromgren | 128/80 C |
| 4,256,097 | 3/1981 | Willis | 128/80 C |
| 4,323,059 | 4/1982 | Rambert et al. | 128/80 C |
| 4,353,361 | 10/1982 | Foster | 128/80 C |

FOREIGN PATENT DOCUMENTS

| | | | |
|---|---|---|---|
| 673387 | 11/1963 | Canada | 128/80 C |
| 2441382 | 7/1980 | France | 128/80 C |
| 2477409 | 9/1981 | France | 128/80 F |

*Primary Examiner*—Charles Pearson
*Assistant Examiner*—Tonya Lamb
*Attorney, Agent, or Firm*—Jerry W. Mills; Alan W. Lintel

[57] ABSTRACT

A knee brace (10) is provided with a thigh collar (12) and a tibia collar (40) for securing the brace to the user's leg. A hinge (20) is connected to the thigh collar (12) and the tibia collar (40) in order to allow extension and flexion of the leg. The tibia collar (40) is connected to the hinge (20) via a connecting rod (26) upon which the tibia collar (40) may rotate and piston vertically. The desired range within which tibia collar (40) may rotate and piston may be adjusted by cams (34 and 36). An elastic wrap (56) is attached to the thigh collar (12) and the tibia collar (40) in order to facilitate proper rotation of the leg.

16 Claims, 1 Drawing Sheet

PIVOTING KNEE BRACE WITH ROTATING AND TRANSLATING TIBIA COLLAR

TECHNICAL FIELD OF THE INVENTION

This invention relates in general to a method and apparatus for supporting a knee and more particularly relates to a method and apparatus for supporting a knee while allowing tibial rotation within a predetermined range.

BACKGROUND OF THE INVENTION

With increasing participation in athletic activities, knee ligament injuries have become more common. Those wishing to participate in athletic endeavors after an injury often use a brace to protect the damaged knee from reinjury. Optimally, the brace will prevent the injured knee from orienting itself in a "subluxed" position, wherein the relation between the tibia and the femur has become skewed away from an anatomically sound or "conjugated" position.

The knee reaches a critical period during the transition from an "unloaded" or "lowload" state (wherein the knee is not supporting any weight) to a "loaded" state (wherein the knee is supporting the body's weight). In order to prevent injury, the tibia and femur must be in a conjugated position at the time of loading. If the knee joint is in a subluxed position at loading, a reflex proprioceptive arc unconsciously causes a reflex inhibition of muscle function, thereby reducing support to the leg and resulting in disabling "giving way" symptoms that occur with unstable knees. Whereas subluxation of the tibia often occurs while the knee is in an unloaded state, it seldom occurs once the knee has become loaded in an anatomically stable position. Hence, the primary function of a brace should be to prevent subluxation while the knee is in an unloaded state.

During flexion and extension of the leg, the tibia rotates about an axis generally parallel to the medial side of the tibia. In the normal rotational mechanics of the knee, the tibia undergoes a progressive external rotation as the knee is brought through the last thirty to forty degrees of extension. This allows for the so-called "screw home" mechanism to occur as the knee reaches terminal extension. During this phase, the rotation of the tibia is most important, since the tibia must reach its proper conjugated position before loading.

Two types of braces have heretofore been available to prevent subluxation of the knee. The first type of brace is a "rigid" brace, in which a rigid thigh piece is linked to a rigid tibial piece by two rigid hinges. Rigid braces attempt to prevent tibial subluxation at full extension by preventing any rotation of the tibia during flexion or extension. Due to the inability to rigidly grasp the involved extremity, some degree of rotation may occur either by the brace shifting on the skin or by the skin envelope shifting around the involved leg. While the rigidity imparted by this type of brace increases the resistance to subluxation of the tibia at terminal extension, it also resists the normal rotations that need to occur during functional activity.

The second type of brace rotates the tibia in a set arc, or degree of motion, during flexion and extension. While these braces allow rotation of the tibia, a predefined path of motion must be set at the factory based on data supplied by the user's physician. Consequently, adjustments to the rotating mechanisms of these braces must also be made at the factory, resulting in inconvenience and expense to the user. Furthermore, these braces have a low margin of error, i.e., if the brace is not perfectly positioned on the user's knee, the tibia will not follow its normal path, and subluxation will result.

Therefore, a need has arisen for a knee brace which allows free rotation of the tibia, yet positions the knee in an anatomically stable position prior to loading. Furthermore, a need exists for a knee brace whose range of rotation may be easily and accurately adjusted by the user or by a qualified physician.

SUMMARY OF THE INVENTION

In accordance with the present invention, a knee brace apparatus is provided which substantially eliminates or prevents the disadvantages and problems associated with prior art knee braces.

In accordance with another aspect of the invention, a knee brace is provided having a first attachment portion for attaching the brace to the user's thigh, a second attachment portion for attaching the brace about the user's tibia, and a hinge connected to the medial side of the first and second attachment portions to allow flexion and extension of the user's leg. The second attachment portion is rotatably attached to the hinge, such that rotation of the tibia about an axis medial and parallel to the tibia is allowed in order to accommodate the normal mechanics of the knee.

In yet another aspect of the invention, the knee brace may be configured such that the rotation of the second attachment portion may be limited to rotation within a predetermined arc.

In a further aspect of the invention, the second attachment portion may move vertically towards and away from the hinge, in order to accommodate normal elongation and contraction of the knee during flexion and extension.

In yet a further aspect of the invention, an elastic wrap is provided in order to facilitate rotation of the tibia towards a conjugated position before loading the knee at full extension.

BRIEF DESCRIPTION OF THE DRAWINGS

For a more complete understanding of the present invention and the advantages thereof, reference is now made to the following descriptions taken in conjunction with the accompanying drawings in which.

DETAILED DESCRIPTION OF THE INVENTION

The preferred embodiment of the present invention is best understood by referring to FIGS. 1-4 of the Drawings, like numerals being used for like and corresponding parts of the various Drawings.

Figure 1:
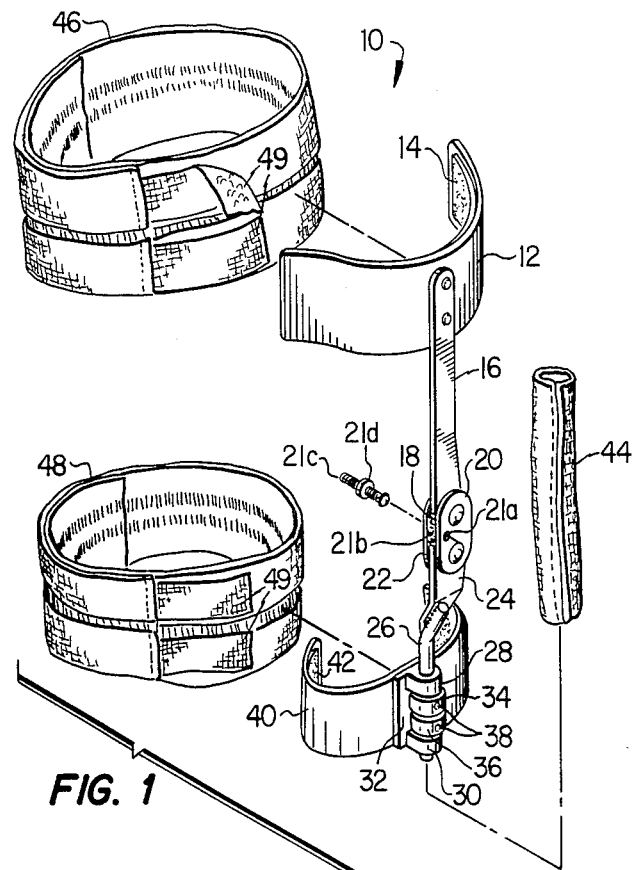
FIG. 1 is a perspective view of a knee brace, with the attachment straps shown in an exploded view.

FIG. 1 illustrates a knee brace 10 used to allow external and internal rotation of the tibia during flexion and extension of the knee, such rotation confined to a predetermined adjustable range. A thigh collar 12, having inner padding 14, is connected to one end of a thigh upright bar 16. The other end of the thigh upright bar 16 forms a first gear 18 used in hinge 20. A complementary second gear 22 is formed out of one end of a Tibia upright bar 24. Two holes 21a-b are placed on the hinge 20. A connecting rod 26 is attached to the other end of the tibia upright bar 24. The connecting rod 26 is disposed through upper and lower mounting sleeves 28 and 30 of mounting plate 32. Upper and lower cams 34 and 36 are mounted on the connecting rod 26. The upper and lower cams 34 and 36 can be fixedly mounted to the connecting rod 26 using set screws 38. The mounting plate 32 is attached to a tibia collar 40 having inner padding 42. The thigh upright bar 16, hinge 20, tibia upright bar 24 and connecting rod 26 are covered with side padding 44. Thigh collar 12 and tibia collar 40 are covered by attachment straps 46 and 48, shown in exploded view. The attachment straps 46 and 48 wrap around the user's leg, and one end of each attachment straps is secured to the body of the strap using fasteners 49.

In operation, the thigh collar 12 is positioned about the user's thigh with the thigh upright bar 16 positioned on the medial (inside) portion of the user's thigh. The thigh collar 12 should be positioned such that the hinge 20 is located beside the medial portion of the user's knee. Likewise, tibia collar 40 is disposed about the medial portion of the user's calf. The thigh collar 12 and tibia collar 40 can be adjusted to provide a snug fit about the user's thigh and calf. If necessary, thigh collar 12 and tibia collar 40 may be bent to provide a proper fit. In the preferred embodiment, the thigh collar 12 and tibia collar 40 are manufactured from a light weight metal which allows the collars 12 and 40 to be bent for greater conformance to the user's leg. However, other suitable resilient materials could be substituted to reach a similar result. Attachment straps 46 and 48 further secure the thigh collar 12 and tibia collar 40 to the user's leg, such that slippage between the collars 12 and 40 and the leg is minimized. In the preferred embodiment, the attachment straps 46 and 48 are manufactured from an elastic material, using a hook and loop fastener 49, such as that sold under the tradename "Velcro," to secure the ends of the attachment straps 46 and 48. Side padding 44 prevents contact between the hinge 20 and the user's leg.

Once the knee brace 10 is fitted to the user's leg, the user will have full range of flexion and extension. Hinge 20 is designed to prevent extension beyond a vertical alignment of the thigh upright bar 16 and the tibia upright bar 24, thus preventing hyperextension of the user's knee. A hinge of this type is described in U.S. Pat. Nos. 4,370,977 and 4,433,679 to Mauldin et al. both entitled "Knee and Elbow Brace".

Holes 21a-b hold an optional mechanism for adjusting the amount of allowed extension. The interior hole 21b is threaded to allow a set screw 21b (shown in exploded view) to be placed through exterior hole 21a and secured in interior hole 21b. A bushing 21d is placed on the set screw 21c between the sides of the hinge 20. As the gears 18 and 22 rotate towards full extension, the bushing 21d, interacts with the end of the gears, thus impeding further rotation. By varying the size of the bushing 21d the amount of extension can be controlled and limited.

Figure 2:
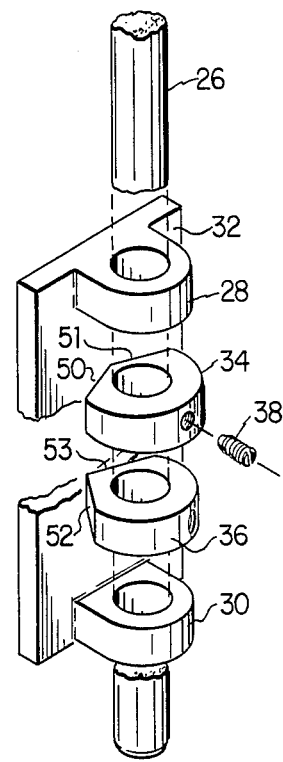
FIG. 2 is a perspective view of the rotatable tibia collar.

An important aspect of the knee brace 10 is its rotating tibia collar 40 displayed in FIG. 2. The connecting rod 26 extends through upper and lower mounting sleeves 28 and 30, within which the connecting rod 26 may freely rotate as well as slide up and down. Two cams 34 and 36 are secured to the connecting rod 26 by set screws 38 in order to restrict the freedom of motion of the connecting rod 26 within the mounting sleeves 28 and 30.

During flexion of the leg, the center of the knee "elongates", resulting in a "pistoning" action of the knee during flexion and extension. Thus, during flexion, a structure for extending the distance between the hinge 20 and tibia collar 40 is necessary.

In the illustrated embodiment, the vertical position of the upper cam 34 determines the maximum distance which may be achieved between the tibia collar 40 and the hinge 20. Once the upper mounting sleeve 28 abuts the upper cam 34, the tibia collar 40 will be unable to move upwardly along the connecting rod 26. Likewise, the vertical position of the lower cam 36 determines the minimum distance between the tibia collar 40 and the hinge 20. Thus, the upper and lower cams 34 and 36 may be adjusted to allow a predetermined pistoning movement range of the tibia collar. The amount of allowable pistoning is controlled by relative positioning of the two cams 34 and 36.

Figure 3:
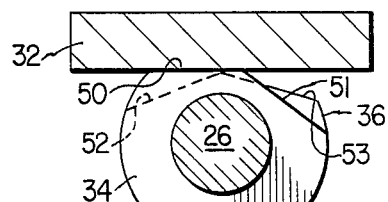
FIG. 3 is a top plan view of the adjustable cams used in the rotatable tibia collar.

The cams 34 and 36 may also be adjusted to control and limit rotation of the tibia collar 40 about the connecting rod 26, as shown in connection with FIGS. 2 and 3. Each cam 34 and 36 has two flattened sides, the upper cam 34 shown with a counter-clockwise stop 50 and a clockwise stop 51 and the lower cam 36 shown with counter-clockwise stop 52 and clockwise stop 53. In the illustrated embodiment of FIG. 3, the cams are positioned such that the counter-clockwise stop 50 of the upper cam 34 limits counter-clockwise rotation of the tibia collar 40 around the connecting rod 26 and the clockwise stop 53 of the lower cam 36 limits clockwise rotation of the tibia collar 40 around the connecting rod 26. As the tibia collar 40 rotates counter-clockwise, the mounting plate 32 will abut the counter-clockwise stop 50 of the upper cam 34 and hence further rotational movement in the counter-clockwise direction will be prevented. Similarly, as the tibia collar 40 rotates in a clockwise rotation, the mounting plate 32 will contact the clockwise stop 53 of the lower cam 36 and further clockwise rotation will be prevented. The cams 34 and 36 may be rotated about the connecting rod 26 so as to define a prescribed arc in which the tibia collar 40 may rotate. Alternatively, the cams 34 and 36 may be set with the corresponding stops aligned such that only clockwise or counter-clockwise rotation is restricted.

While the amount of tibial rotation may vary between individuals, tibial rotation is always present when the knee is functioning in an anatomically correct way. Studies have shown that the axis of rotation for the internal and external rotational aspects of the normal gate cycle is somewhat medial to the medial tibial plateau. Thus, the knee brace 10 is mounted on the user's leg such that the tibial collar 40 rotates about the connecting rod on the medial side of the user's leg, the connecting rod 26 closely approximating the leg's normal axis of rotation. Thus, the knee brace 10 allows the tibia to follow its normal path during flexion and extension.

The adjustable cams 34 and 36 allow for three adjustments: (1) adjusting the vertical position of the tibia collar 40 on the connecting rod 26 to account for varying leg length, (2) adjusting the amount of allowable pistoning by the tibia collar 40 and (3) adjusting the arc about which the tibia collar 40 may rotate.

The first adjustment, adjusting the tibia collar 40 along the user's calf, may be accomplished by loosening the set screws 38 to the cams 34 and 36, and sliding the tibia collar 40 to a point proximate the user's calf, while the hinge 20 is located proximate the middle of the user's knee. The tibia collar 40 should be positioned such that the user feels comfortable with the fit.

After the tibia collar 40 is properly fitted to the user's calf, the allowable amount of pistoning can be set. The amount of desired pistoning may be decreased by separating the two cams 34 and 36 or increased by moving the cams 34 and 36 together. The elongation of the knee center is typically less than one-half of an inch from full flexion to full extension; the exact amount of elongation will depend upon the individual. A proper amount of pistoning may be determined through a trial and error process by choosing a setting and flexing and extending the user's leg to test the correctness of the setting. The setting should be chosen such that at maximum flexion a slight gap exists between the lower cam 36 and the lower mounting sleeve 30, while at maximum extension a slight gap exists between the upper cam 34 and the upper mounting sleeve 28.

The rotational limitation setting is accomplished by rotating one of the cams 34 or 36 such that its counter-clockwise stop 50 or 52 inhibits counter-clockwise rotation of the tibia collar 40 past a certain point, and rotating the other cam 34 or 36 such that its clockwise stop 51 or 53 inhibits clockwise rotation of the tibia collar 40 past a desired point. For a particular individual, the range of allowable rotation will depend upon the nature of the affliction and the particular mechanics of the individual's knee. For example, if the user suffers from an anterior cruciate ligament injury, the cams 34 and 36 could be set such that normal external rotation of the tibia is allowed, but internal rotation past a conjugated position is blocked. Thus, for an anterior cruciate ligament injury, both cams could be set to block internal rotation. Using this setting as a starting point, the physician or user can adjust the cams 34 and 36 so that the brace allows rotation of the tibia necessary for normal movement of the leg, yet prevents excessive rotation which could cause further damage to the ligament. For a posterior cruciate ligament injury, one cam should be set to block internal rotation, and the other cam set to block external rotation.

Figure 4:
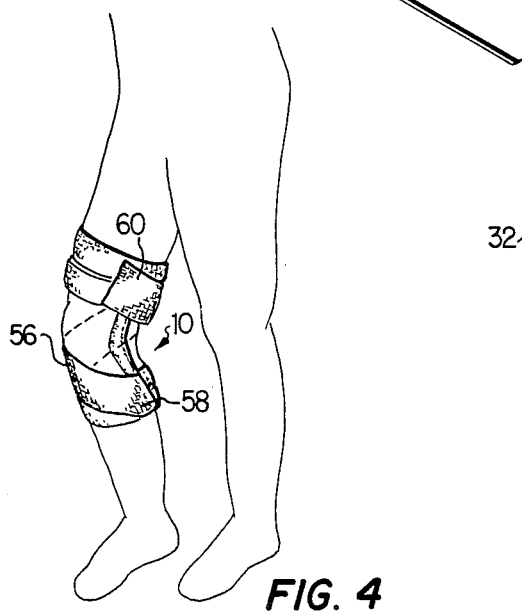
FIG. 4 illustrates attachment of an elastic wrap to the present knee brace.

Referring now to FIG. 4, the knee brace 10 is depicted upon a user's leg, with an elastic wrap 56 connected between the tibia collar 40 and the thigh collar 12. The preferred path of the elastic wrap 56 from the tibia collar 40 to the thigh collar 12 depends upon the affliction of the knee. The illustrated embodiment depicts the use of the wrap 56 in the case of an anterior cruciate ligament injury. A first end 58 of the elastic wrap 56 is fastened to a portion of the lower attachment strap 48 on the medial side of the user's leg and passes around the posterior of the user's leg towards the lateral portion of the user's knee. The wrap 56 continues around the anterior of the user's knee where the second end 60 of the wrap 56 attaches to a portion of the upper attachment strap 46. The exact point of attachment depends upon the length of the strap.

The purpose of the elastic wrap 56 is to rotate the leg towards a conjugated position before the leg is loaded. Thus, if the tibia rotates away from a conjugated position during flexion, the elastic strap should aid the leg muscles in rotating the tibia back to a conjugated position before loading at full extension. It should be noted that were the individual's affliction caused by a posterior cruciate injury, the path of the elastic wrap 56 would be reversed; the first end 58 of the wrap 56 would be attached to the lower attachment strap 48 on the lateral side of the user's leg, wrapped around the posterior of the user's leg toward the medial side of the user's knee, and around the anterior of the user's knee where it is anchored on the upper attachment strap 46.

Preferably, the wrap 56 is attached to the knee brace 10 while the user's leg is positioned for about 50 to 70 degrees of flexion. With the wrap 56 applied at moderate tension with the leg bent at 50° C. flexion, the elasticity should provide a sufficient force to rotate the leg to a conjugated position before the leg is loaded at full extension.

In the preferred embodiment, the wrap 56 is attached to the attachment straps 46 and 48 through use of a hook and loop fastener, such as that sold under the trade name "Velcro," providing easy application and removal of the wrap 56.

While the use of an elastic wrap 56 is shown in the preferred embodiment, other means of providing a counter-rotational force, such as a spring-loaded mechanism, could be substituted by one skilled in the art to aid in positioning the tibia in a conjugated position before loading.

Although the present invention has been described in detail, it should be understood that various changes, substitutions and alterations can be made therein without departing from the spirit and scope of the invention as defined by the appended claims.

What is claimed is:

1. A knee brace comprising:
    a first attachment means for attaching the brace to a portion of the user's body above the knee;
    second attachment means for attaching the brace about the user's tibia, said second attachment means including a rigid plate, a mounting sleeve attached to said plate, and a rod slideably and rotatably engaged within said mounting sleeve and disposed on an axis medial to the user's leg;
    first and second limiting means adjustably attached to said rod for impeding rotational movement of said plate around said rod in a first and second rotational direction at a first and second predetermined radial position; and
    a hinge connected to said first and second attachment means, said hinge having means for allowing flexion and extension of the user's leg.

2. The knee brace of claim 1 and further comprising resilient means for providing a rotational force to said second attachment means to aid in proper alignment of the user's tibia and femur at full extension of the user's leg.

3. The knee brace of claim 1, wherein said second attachment means is operable to move vertically along said axis.

4. The knee brace of claim 3, further comprising means for limiting the amount of vertical motion along said axis.

5. The knee brace of claim 4, wherein said means for limiting comprises upper inhibiting means for inhibiting movement of said lower attachment means beyond a first predetermined vertical position on said axis and lower inhibiting means for inhibiting movement of said lower attachment means beyond a second predetermined vertical position on said axis.

6. The knee brace of claim 1, wherein said first limiting means comprises a collar member rotatably disposed on said rod having an inhibiting portion for contacting said rigid plate at said first predetermined radial position; and means for securing said collar member to said rod.

7. The brace of claim 3 wherein said collar member is adjustably attached to said rod such that the radial position at which contact occurs between said collar member and said plate may be adjusted by the user and fixedly attached to said rod using a set screw.

8. The brace of claim 6 wherein said mounting sleeve comprises a first mounting sleeve and further comprising a second mounting sleeve in which said rod is slideably and rotatably engaged, said collar member disposed between said mounting sleeves such that axial and rotational movement of said plate on said rod is limited within a predetermined range.

9. A knee brace for maintaining a proper relationship between the user's tibia and femur comprising:

first attachment means for attaching the brace about the user's femur;

a hinge having an upper and lower support for allowing flexion and extension of the user's leg, said upper support connected to said first attachment means;

second attachment means for attaching the brace about the user's tibia, said second attachment means including a rigid plate slideably and rotatably engaged on said lower support; and limiting means adjustably connected to said lower support and operable to prevent rotation of said plate on said lower support beyond first and second predetermined radial positions by contacting said rigid plate.

10. The knee brace of claim 9, wherein said first and second stopping means each comprise an annular member slideably engaged on said lower support, said annular member having two flat sides, each of said flat sides defining a plane substantially parallel to said lower support.

11. The knee brace of claim 9, wherein said rotational limiting means comprises first and second stopping means, said first stopping means operable to prevent clockwise rotation of the second attachment means about the lower support past a first predetermined radial position and said second stopping means operable to prevent clockwise rotation of the second attachment means about the lower support past a second predetermined radial position.

12. The knee brace of claim 11, wherein said first and second stopping means are independently adjustable such that the range of rotation of said second attachment means can be varied by adjusting the position of said first and second stopping means about said lower support.

13. A knee brace for maintaining a proper relationship between the user's tibia and femur comprising:

femoral attachment means for attaching the brace about the user's femur;

tibial attachment means for attaching the brace about the user's tibia, said tibial attachment means including a rigid plate having a plurality of mounting collars;

a hinge having a femoral and a tibial support, said femoral support connected to said femoral attachment means and said tibial support slideably and rotatably engaged in said mounting collars;

extension limiting means for limiting the degree of extension of the user's leg provided by said hinge;

first and second stopping means independently adjustably engaged on said tibial support between said mounting collars for preventing rotation of said tibial attachment means past first and second predetermined radial positions on said tibial support while allowing rotation of said tibial attachment means between said first and second radial positions by contacting said rigid plate at said first and second positions and for confining axial movement of said tibial attachment means to the portion of said tibial support between first and second predetermined axial positions on said tibial support by contacting said mounting collars; and resilient means for providing a rotational force in opposition to rotational movement away from a third predetermined radial position, said resilient means operable to facilitate orientation of the user's tibia in a conjugated position at terminal extension.

14. The knee brace of claim 13, wherein said resilient means comprises an elastic wrap.

15. The brace of claim 13 wherein said hinge comprises interactive gear portions, and said extension limiting means comprises a bushing disposed between said gear portions such that said gear portions interact with said bushing at a predetermined angle of extension.

16. The brace of claim 13, and further comprising straps attached to said femoral and tibial attachment means to adjustably wrap around the user's leg.

* * * * *